(12) United States Patent
Easterling

(10) Patent No.: US 11,854,778 B2
(45) Date of Patent: Dec. 26, 2023

(54) MASS SPECTROMETRY IMAGING WITH SUBSTANCE IDENTIFICATION USING ION MOBILITY

(71) Applicant: Bruker Scientific LLC, Billerica, MA (US)

(72) Inventor: Michael Easterling, Billerica, MA (US)

( * ) Notice: Subject to any disclaimer, the term of this patent is extended or adjusted under 35 U.S.C. 154(b) by 49 days.

(21) Appl. No.: 18/149,189

(22) Filed: Jan. 3, 2023

(65) Prior Publication Data

US 2023/0135091 A1    May 4, 2023

Related U.S. Application Data

(63) Continuation of application No. 16/705,403, filed on Dec. 6, 2019, now Pat. No. 11,569,078.

(51) Int. Cl.
| | |
|---|---|
| *H01J 49/00* | (2006.01) |
| *G01N 27/622* | (2021.01) |
| *G01N 30/72* | (2006.01) |
| *G01N 33/50* | (2006.01) |
| *G01N 33/68* | (2006.01) |
| *H01J 49/16* | (2006.01) |
| *G01N 33/483* | (2006.01) |

(52) U.S. Cl.
CPC ........ *H01J 49/0004* (2013.01); *G01N 27/622* (2013.01); *G01N 30/7233* (2013.01); *G01N 33/50* (2013.01); *G01N 33/6848* (2013.01); *H01J 49/0031* (2013.01); *H01J 49/164* (2013.01); *H01J 49/165* (2013.01); *G01N 33/4833* (2013.01); *G01N 2560/00* (2013.01)

(58) Field of Classification Search
CPC ........ H01J 49/00; H01J 49/02; H01J 49/0004; H01J 49/0031; H01J 49/164; H01J 49/165; H01J 49/26; H01J 49/42; H01J 49/421; H01J 49/422; H01J 49/4225; G01N 27/622; G01N 30/7233; G01N 33/6848; G01N 33/50; G01N 33/4833; G01N 2560/00
USPC ................................ 250/281, 282, 290, 293
See application file for complete search history.

(56) References Cited

U.S. PATENT DOCUMENTS

| | | | |
|---|---|---|---|
| 2014/0329274 A1* | 11/2014 | Bowen ................... | G01N 33/58 250/281 |
| 2017/0178887 A1* | 6/2017 | Park ...................... | H01J 49/066 |
| 2017/0350861 A1* | 12/2017 | Harder ............... | G01N 30/7233 |

* cited by examiner

*Primary Examiner* — Jason L McCormack
(74) *Attorney, Agent, or Firm* — Benoit & Côté Inc.

(57) ABSTRACT

A method for the identification and localization of small molecule species in a histologic thin tissue section comprises the steps of: a) acquiring a mass/mobility image of the tissue section and generating a mass/mobility map of the small molecule species of interest for each pixel of the image; b) providing a second sample of the same tissue and extracting the small molecules of interest, separating them, and acquiring mass and ion mobility spectra from the separated small molecules; c) identifying the small molecules of interest using corresponding reference databases; and d) assigning identified small molecules to entries in the mass/mobility maps of the first tissue section by comparison of ion masses and mobilities of the identified species to those of the second thin tissue section.

14 Claims, 2 Drawing Sheets

MASS SPECTROMETRY IMAGING WITH SUBSTANCE IDENTIFICATION USING ION MOBILITY

BACKGROUND OF THE INVENTION

Field of the Invention

The invention relates to mass spectrometry imaging of histologic thin tissue sections, particularly to the identification of small molecules within the images.

Description of the Related Art

The term "mass spectrometric image" of a thin tissue section which is obtained by mass spectrometry imaging (MSI) is used here for an image which contains a mass spectrum with molecular information for every image point, called a "pixel". The "mass spectrometric image" thus corresponds precisely to an "unreduced color image" which contains a full color spectrum for every image point.

A trend in mass spectrometry points to the implementation of ion mobility separators. If imaging mass spectrometers become equipped with ion mobility separators, "mass/mobility imaging" becomes possible, with maps for precise masses and ion mobilities for each pixel. There is no easy optical correspondence to "mass/mobility imaging".

Mass spectrometry with ionization of the samples by matrix-assisted laser desorption (MALDI) has been used successfully for many years for the determination of precise molecular masses, and for the identification of biological substances, particularly proteins and peptides. This type of analytical technique can also be used for complex mixtures with some success.

In mass spectrometry imaging, a direct identification of proteins, endogenous peptides, metabolites of natural substances or pharmaceuticals, glycans and lipids from a thin tissue section is so far only possible in rare cases; their identification therefore requires additional measures. In non-imaging mass spectrometry, these measures usually entail a fragmentation of the proteins or their ions to increase the information content, either fragmentation of the protein molecules by enzymatic digest, or fragmentation of selected parent ions for the generation of fragment ions, or even combinations of both. Proteolytic peptides (sometimes called "digest peptides"), measurable between 800 and 4,000 atomic mass units, are peptides which result from the enzymatic degradation of the protein chain, e.g. by digestion with the protease trypsin. Large portions of the amino acid sequence can be read from fragment ion mass spectra; this makes an identification of these proteins possible. The methods for acquiring fragment ion mass spectra consume, however, considerable quantities of substance; for mass spectrometric imaging, the amount of substance of an image point ("pixel") is hardly sufficient for a fragment ion spectrum acquisition. In addition, ionization by matrix-assisted laser desorption (MALDI) as mostly used for mass spectrometry imaging, produces mainly only singly charged ions, the fragmentation of which is more difficult, insensitive and does not deliver much information. Up to now, attempts at generating fragment ion spectra showed that daughter ion spectra of moderate quality can be obtained from one or sometimes two high-intensity peptides of an image point, but this is by no means sufficient for a substance identification on a larger scale.

An advanced method to identify proteins in thin tissue sections by mass spectrometry has been published in U.S. Pat. No. 10,197,576 B2 (Suckau et al), which is incorporated herein by reference. The method uses two similar tissue sections, and digests the proteins in both sections by a suitable enzyme while substantially preserving the biomolecule positions in the tissue sections. One section is used to acquire mass images of the digest peptides with precise masses of the peptides in each pixel generating a peptide map for each pixel. From the other section, the digest peptides of the whole tissue section are extracted and analyzed by liquid chromatography with tandem mass spectrometry (LC/MS/MS), with ionization by electro spraying, yielding protein identifications by fragment ion spectra of the digest peptides. In particular, peptides are identified by: (1) retention time; (2) precise mass; and (3) ion fragmentation pattern. If the masses of the peptides belonging to a particular protein are compared to the digest peptide masses of the peptide maps in one of the pixels, and the comparison reveals several mass concordances, this protein is regarded to be more or less safely identified, depending on the number of mass concordances.

The Suckau patent describes in detail the preparation of the thin tissue sections, the digestion procedure, and the identification process. This method, however, is primarily directed to the identification and local distribution of larger proteins in the tissue sections. There is still a need for the correct identification of glycans, lipids, endogenous peptides, metabolites, pharmaceuticals or other smaller molecules. The identification in the mass spectral image by precise masses alone appears to be not safe enough.

SUMMARY OF THE INVENTION

Modern mass spectrometers are frequently equipped with ion mobility separation devices which allow measuring the ion mobility and separating the ions according to their ion mobility. The present invention makes use of such a spectrometer, and determines collisional cross sections (CCS) of ions using measured ion mobilities. For a large molecule, the collisional cross section gives information about the folding structure of the molecule while, for a small molecule, the collisional cross section constitutes an additional characteristic property that can be used, in connection with the measurement of the precise mass, to identify a particular molecular ion. In an exemplary embodiment of the invention, measurements of collisional cross sections (or simply ion mobility values) and precise masses are used to identify substances with lower molecular weights, and to investigate their distribution in thin tissue sections.

In a method according to the invention, small molecules are identified and localized in a histological thin tissue section that represents a first sample of a subject tissue. A second sample of the subject tissue may be a similar thin tissue section, while in an alternative embodiment a second tissue sample may be larger than the thin tissue section. Since small molecules are to be investigated, enzymatic digestions do not need to be applied. The first sample tissue section serves to measure the mass spectral image, using ionization by matrix-assisted laser desorption and building maps of the precise masses of all smaller molecules in each pixel. But differently from the method of the cited patent, the ion mobilities of all ion types are measured as precisely as possible and included in the maps.

From the second sample of the tissue, which may also be a thin tissue section or a larger piece of tissue, all soluble substances are extracted, and the substances of the solution are separated by a separation method such as liquid chromatography. The second tissue sample is not, however, limited to being a single piece of tissue; as an example, about 10 to 20 thin tissue sections may be used as a larger second tissue sample. Electrospray ionization of the extracted and LC separated substances generates multiply charged ions. A mass spectrometer with built-in ion mobility spectrometer measures precise masses and ion mobilities, and these measured values are compared to a suitable reference database to create a list of identified substances. The list of identified substances with precise masses and ion mobility values generated by the second sample of tissue is then used for the identification of the small molecules in the pixels of the mass spectral image of the thin tissue section.

Ions in the range of 100 to about 4000 Daltons may be identified by a combination of their retention times in the separation method, their collisional cross sections, and their precise masses, which are compared with reference data from a suitable database. The database may be taken from the internet or built or completed by the user. In the mass maps of the pixels of the thin tissue section, ions of interest are then identified by precise masses and collisional cross sections using the list of small molecules safely found in the second tissue sample.

In another embodiment of the invention, the thin tissue section is used as both the first and second tissue samples. As in other embodiments, the tissue section is first used to measure a mass spectral image with ion mass and ion mobility maps per pixel, but enough material is left to extract, in a second step, the substances of interest. In this way, the tissue section can also serve as the second tissue sample, and solving the remaining matrix material generates a solution also containing all small molecules which then can be separated and identified as described above.

A particularly advantageous embodiment bases the identification of the small molecules of the second tissue sample on a measurement using liquid chromatography, ion mobility spectrometry and tandem mass spectrometry (LC-IMS-MS-MS), i.e., fragment ion spectra may be generated additionally and used to provide a more precise identification. The ionization is performed by electrospray, generating multiply charged ions well suited for fragmentation. The ion mobility separation and measurement may be performed by "Trapped Ion Mobility Spectrometry" (TIMS). This method of identifying substances has become known under the name "PASEF" (parallel accumulation, sequential fragmentation). Today, PASEF is the most powerful identification method for substances in tissues. Another embodiment includes an enzymatic digestion to measure proteins in the same measurement run, or to split glycans from glycoproteins or proteoglycans.

The method uses a mass spectrometer with a MALDI ion source and built-in ion mobility spectrometer to measure the mass spectrometric image of the first thin tissue section. For the LC-MS measurements of the second sample, an electrospray ion source should be used, but it is also possible to combine liquid chromatography with MALDI ionization. There are time-of-flight mass spectrometers with orthogonal ion input (OTOF) on the market which are equipped with both types of ion sources (MALDI and ESI) and with an ion mobility spectrometer. Usually, MALDI-TOF instruments with axial ion input are not equipped with ion mobility spectrometers.

For the identification and localization of lipids, glycans, endogenous peptides, metabolites or other smaller molecules of a histologic thin tissue section, the invention provides a first method comprising the following steps: a) acquiring a mass spectrometric image of the substances of the thin tissue section with a mass spectrometer having a built-in ion mobility spectrometer, and generating maps of precise masses and ion mobility values for small molecules of interest for each pixel of the image; b) providing a second sample of the subject tissue and extracting the soluble molecules of the second sample, separating said soluble molecules and analyzing said soluble molecules using a mass spectrometer with built-in ion mobility spectrometer to acquire precise masses and ion mobilities of small molecular ions formed from the soluble molecules; c) identifying the small molecules in the second tissue sample by comparing the retention times of the separation method, the precise masses and the ion mobility values of the ions with reference data, and creating a list of identified small molecules; and d) assigning identified small molecules in the list to entries in the mass/mobility maps generated in step (a) according to mass and ion mobility.

The invention provides an elegant method for the identification and localization of lipids, endogenous peptides, metabolites, glycans or other smaller molecules of a histologic thin tissue section. An additional pre-preparation is applicable to samples containing glycoproteins or proteolipids, where the glycans and lipids are the substances of interest. To cleave glycans or lipids from proteins, enzymatic or chemical methods may be used directly on both tissue samples before the above methods are performed.

The various methods favorably use an orthogonal time-of-flight mass spectrometer comprising an electrospray ion source, a MALDI ion source, and an ion mobility spectrometer for both steps (a) and (b). The ion mobility spectrometer may be a TIMS (trapped ion mobility spectrometer), with which it is possible to use temporal zoom to increase the resolution of the mobility spectrometer, if the target molecules are known beforehand. In this way, isomers with very similar collisional cross sections may be safely separated.

The acquisition of the mass/mobility image in step (a) may be performed, after application of a matrix substance layer, with ionization by matrix-assisted laser desorption in a mass spectrometer comprising an ion mobility separator. In step (b) liquid chromatography or capillary electrophoresis may be used as the separation method. Usually, the substances eluting from the liquid chromatograph or electrophoresis capillary are ionized by electrospray, generating multiply charged ions in addition the singly charged ions. These ions can be fragmented in suitable mass spectrometers, and the fragment ion spectra may be used for the identification of the substances, enlarging the quality of the identification.

In one version of the invention, the separation of the small molecule species is performed by liquid chromatography, with the separated fractions of the eluate being prepared together with a matrix substance as individual samples on one or more MALDI sample support plates. In this version, the mass and mobility spectra of the small molecule species are measured in a mass spectrometer equipped with a MALDI ion source and a mobility spectrometer.

Other variations on the invention include the filtering of wrongly assigned identities by investigation of the distribution of small molecule species of interest on the thin tissue section with respect to homogeneously covered areas of those species, and subsequent removal of widely isolated species. It is also possible, in the analysis of several thin tissue sections of the same tissue, to carry out the steps (b) and (c) only once, and to use the small molecule list obtained in step (c) for the assignment to the species of the mass/mobility images of all thin tissue sections. Finally, the method of the invention may be applied to tissue sections with or without chemical stabilization.

DETAILED DESCRIPTION

Using a mass spectrometer equipped with an ion mobility separation device, a method according to the invention involves separating the ions according to their ion mobility and measuring corresponding ion mobility values. From these values, collisional cross sections (CCS) are then calculated. As mentioned above, the collisional cross sections give information about the folding structure of the molecule, in most cases showing different isomers with different folding structures and different collisional cross sections. Small molecules usually present only one single isomer with one single collisional cross section, but the collisional cross section constitutes an additional characteristic property that can be used, in connection with a measurement of the precise mass, for an identification of a molecular ion. In accordance with the invention, a measurement of the collisional cross section is used together with precise masses to identify substances with lower molecular weight and investigate their distribution in mass spectral images of thin tissue sections.

Figure 1:
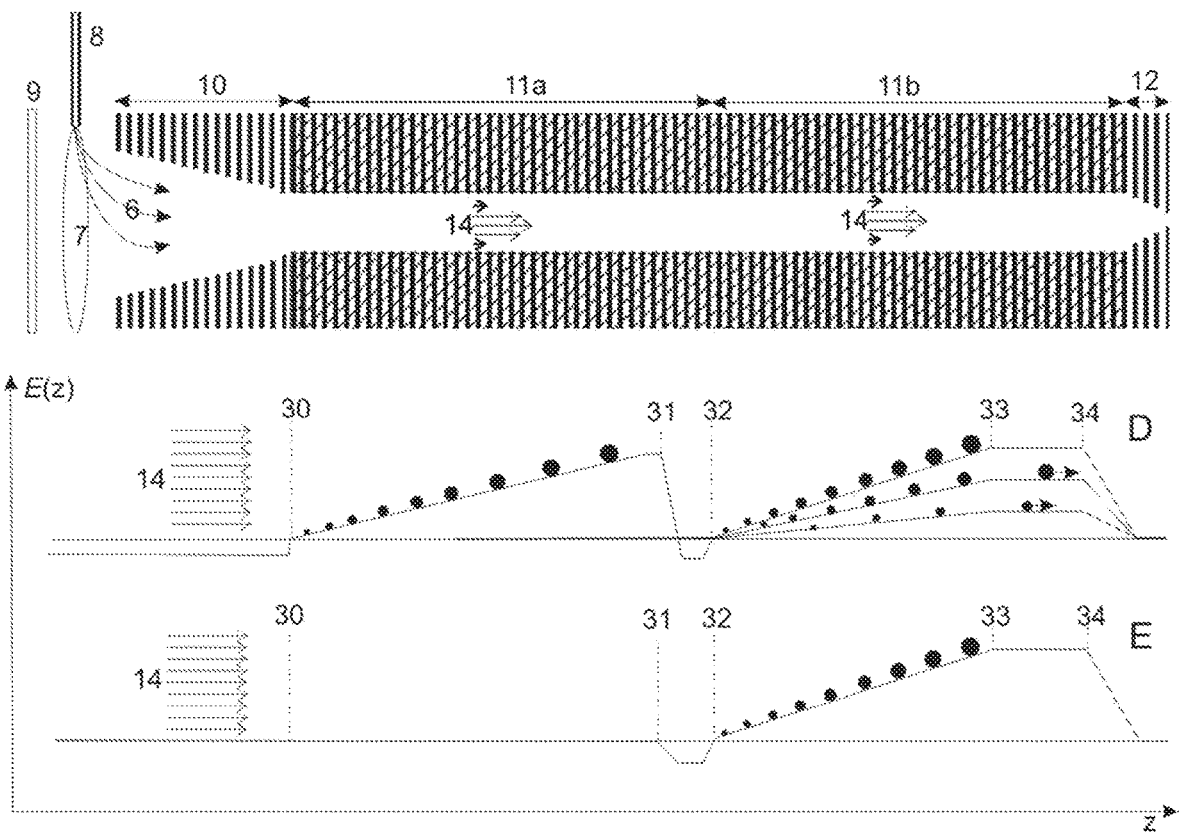
FIG. 1 is a composite figure that schematically depicts a trapped ion mobility spectrometer (TIMS) that may be used with the present invention, with adjacent electric field diagrams showing how electric field strength faced by the ions changes along the length of a drift tube of the TIMS.

A mass spectrometer that may be used with the invention makes use of an ion mobility spectrometer which, in an exemplary embodiment, is a trapped ion mobility spectrometer (TIMS) with parallel ion accumulation, like that shown in FIG. 1. The TIMS shown in the figure includes an RF quadrupole ion tunnel that is divided into ion accumulator unit 11a that is followed by an ion mobility scan unit 11b. In this embodiment, two ion sources are provided, an electrospray source ionization (ESI) source and a matrix-assisted laser desorption ionization (MALDI) source. The ESI source includes a spray capillary 8 that generates ions 6 in a spray plume 7. The MALDI ion source includes a sample support 9 on which a sample material and energy-absorbing matrix are irradiated with a laser (shown in FIG. 2), causing ablation and desorption of the sample and matrix material. These types of ionization sources are known in the art, and are therefore not discussed herein in more detail.

Ions produced from one of the ion sources, such as electrospray ions 6, enter the TIMS via ion funnel 10, and are aligned along an axis thereof by a quadrupolar RF field. The TIMS comprises two DC voltage supply units and resistor chains between electrodes of the system (not shown) for generating two controllable electric field barriers in the axial direction within the two respective tunnel units. A gas flow 14 drives the ions towards an exit but, during an initial accumulation period shown in electric field diagram "D" of FIG. 1, motion of the ions is opposed in the accumulator region 11a by a first DC electric field ramp having a field strength E(z) that increases toward the TIMS exit. During the accumulation period, the DC field ramp has a field strength that increases along the length of the accumulator unit 11a from a minimum value at position 30 to a maximum value at position 31. As is known in the art, minimum and maximum values of the DC field ramp are chosen such that ions 6, under the force of the constant gas flow 14, spread out along the ramp according to ion mobility resulting in a separation of ions along the length of the accumulator unit 11a by ion mobility.

Ions accumulated in the accumulator unit are subsequently released to the scan unit 11b by lowering the electric field barrier in the accumulator unit and allowing the ions to thereby travel to the scan unit 11b under the force of the gas flow 14, as shown in electric field diagram "E" of FIG. 1. In the scan unit 11b is a second DC field barrier, also in the form of a ramp and, as in the accumulator unit 11a, the ions align themselves along the ramp of the barrier according to ion mobility. This balance is achieved relatively quickly due to the prior ion mobility separation in the accumulator unit and, once the ions have been transferred to the scan unit 11b, the field barrier in the accumulator unit is again raised, so that a new group of ions can be introduced and separated. In the scan unit 11b, the ions are progressively scanned out of the scan unit 11b by gradually lowering the electric field barrier ramp. This results in the ions exiting the scan unit under the force of the gas flow 14, the progression of the release being from the ions of the lowest mobility to those of the highest ion mobility. They pass through output ion funnel 12 and into the mass spectrometer downstream.

Figure 2:
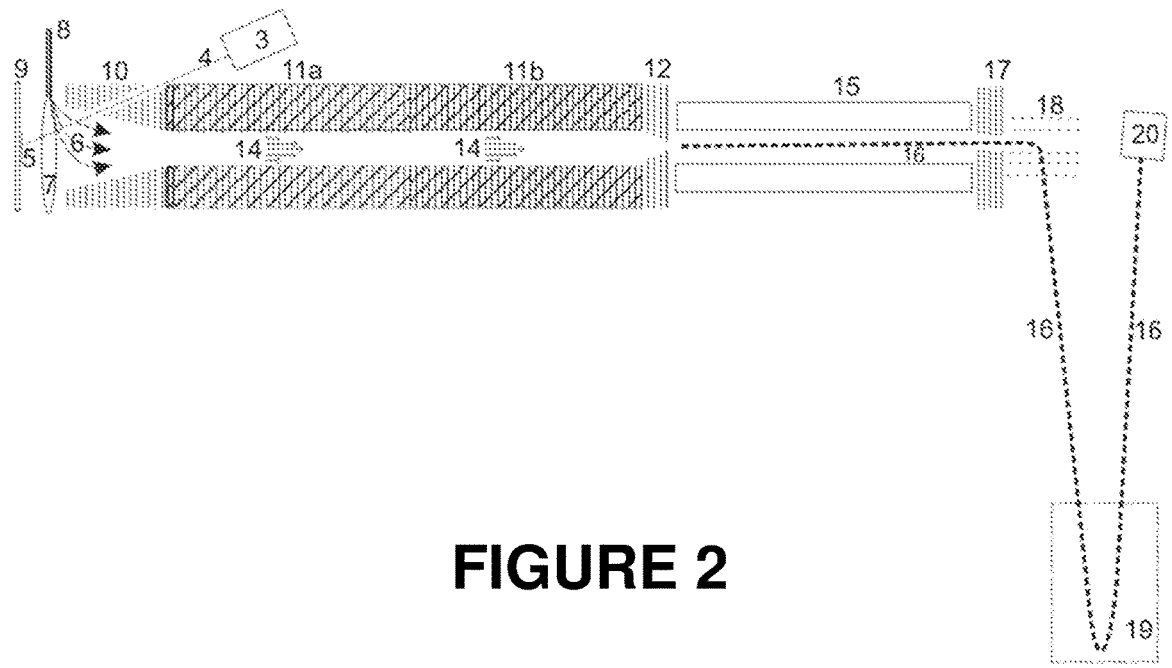
FIG. 2 schematically depicts a time-of-flight (TOF) mass spectrometer that can be used for the method of the invention, and that includes a TIMS like that shown in FIG. 1.

FIG. 2 shows an orthogonal time-of-flight (TOF) mass spectrometer that includes the TIMS of FIG. 1. In this figure, a UV pulse laser 3 and laser beam 4 of the MALDI ion source are shown irradiating a sample 5 on the movable sample support plate 9, and the ESI ion source is also shown, although those skilled in the art will understand that only one of the two ion sources is typically operational at any given time. Downstream of the TIMS is a quadrupole mass filter 15, which can be used for filtering ions input to the mass spectrometer by mass, and/or as a fragmentation chamber in which larger ions are fragmented by ion collisions with a collision gas. The TOF mass spectrometer comprises an ion lens system 17 that focuses the ions of the ion beam 16, and an orthogonal pulser 18 for orthogonally accelerating the ions toward an ion reflector 19. As is known in the art, the orthogonally accelerated ions 16, are reflected by ion reflector 19 and redirected toward an ion detector 20, the output of which is used to produce a mass spectrum.

U.S. Pat. No. 10,197,576 B2 provides an identification method that is based on the multiplicity of digest peptide masses generated from the same large protein. In contrast to that method, the present invention is directed to the identification of smaller molecules like glycans, lipids, endogenous peptides, metabolites, pharmaceuticals or other smaller molecules, which cannot be accurately identified by precise masses alone. With the exception of splitting off the lipid or glycan groups from lipoproteins or glycoproteins, enzymatic digestions do not need to be applied. As in the cited patent, a mass spectral image of a thin tissue section is measured, using MALDI ionization and the building of maps of the precise masses of all smaller molecules in each pixel. But unlike the method of the cited patent, a mass spectrometer with ion mobility separator is used and the collisional cross sections of all ion types are measured and included in the mass maps of the pixels.

In the exemplary embodiment of the invention, using a second tissue sample, all soluble substances are extracted, and the solution is investigated by liquid chromatography-mass spectrometry in a mass spectrometer with ion mobility separation (LC-IMS-MS). Ions in the range of 100 to about 4000 Dalton are then identified by a combination of (1) LC retention time, (2) precise mass and (3) collisional cross section, using reference data. A list of small molecules present in the tissue is generated. In the mass maps of the pixels of the mass spectral image, ions from the list may then be identified using precise masses and collisional cross sections for identification. In this way, the local distribution of glycans, lipids, endogenous peptides, metabolites, pharmaceuticals or other smaller molecules in the mass spectral image may be investigated.

Figure 3:
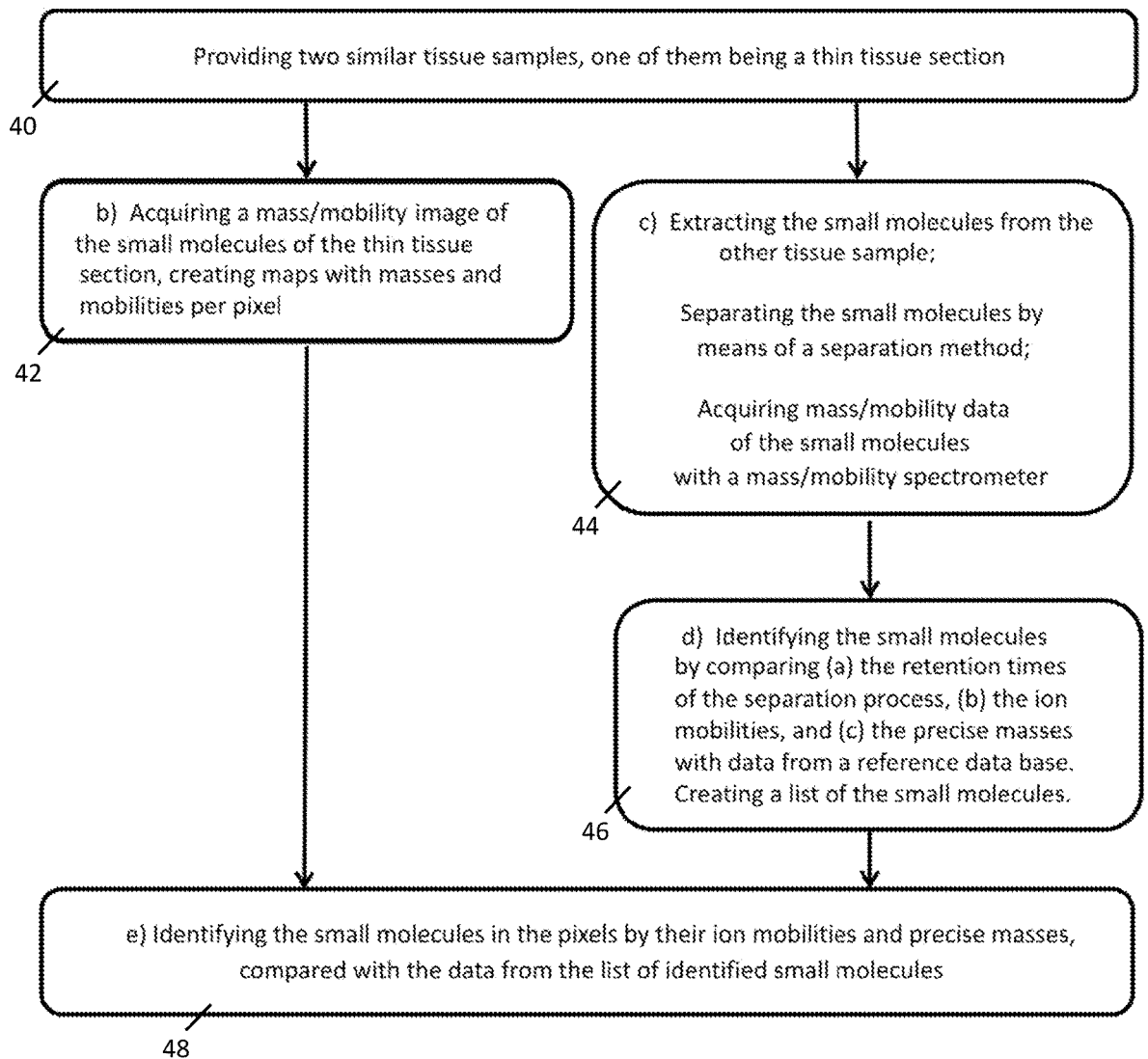
FIG. 3 is a flow diagram that presents a basic work flow of the method of the invention.

The general steps of the invention are shown in FIG. 3, with different embodiments of the method involving variations from the basic work flow. As shown in step 40, the method relies on two similar tissue samples, a first of which is a thin tissue section. In different embodiments of the invention, the second tissue sample may be a second thin tissue section, multiple thin tissue sections, a larger piece of similar tissue, or even a reutilization of the first tissue section. In step 42, a mass/mobility image of the small molecules of the first sample (a thin tissue section) is acquired, with the masses and mobilities being mapped to the pixels of the image. In step 44, the small molecules are extracted from the second tissue sample, and are separated using a separation method, such as liquid chromatography. A mass/mobility spectrometer like that of FIG. 2 is then used to acquire mass/mobility data from the small molecules.

The data acquired in step 44 is used in step 46 to identify the small molecules by comparing the retention times of the separation process, the ion mobilities and the precise masses with data from a reference database of known small molecules. A list of the identified small molecules is then generated. Using this list, the small molecules of the tissue section are identified relative to their pixel locations by comparison of ion mobilities and precise masses in step 48.

As mentioned above, different embodiments of the invention may be used depending on the specific application and circumstances involved. In a very simple and economical embodiment of the method, only a single thin tissue section is used to provide the two tissue samples. In a first step (step 42 in FIG. 3), a mass spectral image with mass and ion mobility maps per pixel is acquired from the tissue section. The measurement of the mass spectral image, however, is done in a manner that leaves enough material to extract, in a second step (step 44), for a LC-IMS-MS measurement. When the first step is performed using MALDI ionization, a removal of the matrix material in the second step according to known solving methods usually also extracts the small molecules of interest embedded therein. The solution of matrix material and small molecules then is separated by liquid chromatography, electrophoresis or another separation method for solved substances. Identification of the small molecules is then performed (step 46) using a reference database containing the separation retention times, the precise masses, and the collisional cross sections of the substances of interest.

In another embodiment, used for higher sensitivity, two similar thin tissue sections are used. The second tissue sample should be a tissue section which is as similar as possible to the first sample tissue section, with the same proportions of all tissue types. It is advantageous, for example, if the second sample thin tissue section is from a nearby cut and, if possible, even an adjacent thin section.

Yet another embodiment includes an enzymatic or chemical digestion to cleave glycans from glycoproteins or proteoglycans, or lipids from lipoproteins. Methods of digestion with preservation of the position of the substance molecules are described in some detail in U.S. Pat. No. 10,197,576 B2 cited above. If two thin tissue sections are used, the cleavage has to be done on both thin tissue sections, and it is essential that any chemical or enzymatic digestion is done in the same way for both thin tissue sections. It is highly advantageous, for example, to apply the same spray and incubation processes to two adjacent thin tissue sections side by side in order to achieve cleaving as similar as possible.

For acquiring the mass spectrometric image, the method uses a desorption ion source like MALDI or desorption electrospray ionization (DESI) and a mass spectrometer with built-in ion mobility separation device. For a LC-MS measurement of the second tissue sample, an electrospray ion source may be used, but it is also possible to combine liquid chromatography with MALDI ionization. A particularly elegant method for these measurements uses liquid chromatography to separate the small molecules extracted from the second tissue sample, and applies separated fractions of the eluate together with the matrix substance as individual samples on one or more MALDI sample support plates. Between 384 and 1536 samples are typically produced in this way, and commercially manufactured pipetting robots may be used for this task, which are coupled with liquid chromatographs and automatically coat the sample support plate. It is then possible to automatically measure the mass spectra of the small molecules from the samples on the sample support in a MALDI time-of-flight mass spectrometer equipped for measuring ion mobilities with corresponding control programs. Unlimited time (until all the sample material is used up) is then available, in principle, for the measurement of the samples, which can each contain several small molecule species. Such a method (without the ion mobility spectrometer) is described in detail in U.S. Pat. No. 7,070,949 B2 (D. Suckau et al.), and has become known under the abbreviated name "LC-MALDI".

In the present invention, the use of LC-MALDI for measuring the second tissue sample provides the advantage that the small molecules of both tissue samples are ionized by the same ionization process. Thus, if the ion mobilities or other characteristics of the spectra are influenced by the ionization process, this influence is the same for the samples of both thin tissue samples.

As discussed above, the exemplary embodiment of the invention uses a mass spectrometer with a built-in ion mobility spectrometer, which may be a TIMS. TIMS is advantageous in that the ion mobility resolution can be easily adjusted for different applications. For example, ion mobilities of different small molecules with exactly the same mass are sometimes very similar. The use of a TIMS allows for easy adjustment of the scan speed which, in turn, allows the ion mobility resolution to be changed as necessary to distinguish small molecules with closely similar ion mobilities, such as isomers with similar collisional cross sections. For example, in a targeted analysis of small molecules with very similar ion mobilities known beforehand, or to measure the collisional cross section as precisely as possible, TIMS allows zooming the ion mobility resolution around the ion mobilities of pairs of small molecules with very similar ion mobilities by controlling the scan speed from fast to slow and back to fast. In a single scan, even more than one pair of molecule types may be zoomed in a single scan.

For the identification and localization of lipids, endogenous peptides, metabolites, glycans or other smaller molecules of a histologic thin tissue section, the invention provides a first basic method comprising the following steps: a) a first tissue sample consisting of a thin tissue section and a second tissue sample from the same overall tissue material as the first tissue sample are provided; b) a mass/mobility image of the substances in the first thin tissue section is acquired, using a MALDI mass spectrometer with built-in ion mobility spectrometer, determining and storing a map of precise masses and ion mobilities for some or all ion species in each pixel; c) all soluble molecules are extracted from the second tissue sample, separated by a chromatographic or electrophoretic separation method and investigated by a mass spectrometer with built-in ion mobility spectrometer, which acquires masses and ion mobilities of small molecules in the mass range from 200 to 4000 Dalton; d) the small molecules of the second tissue sample are identified by comparing the retention times of the substance separator, the precise masses, and the ion mobilities of the ions of the second tissue sample with reference data in a suitable database, whereby a list of glycans, lipids, endogenous peptides, metabolites, pharmaceuticals, metabolites or other smaller molecules is created; and e) the identity of some or all identified molecules in the list are assigned, on the basis of their precise masses and their ion mobilities, to the entries in the mass/mobility maps of the pixels of the mass spectrometric image of the thin tissue section of the first tissue sample which have the same mass and ion mobility. As a result, distributions of these small molecules in the thin tissue section can be graphically presented and correspondingly investigated.

The invention additionally provides a second method for the identification and localization of lipids, endogenous peptides, metabolites, glycans or other smaller molecules of a histologic thin tissue section, comprising the following steps: a) providing a single thin tissue section and preparing it for imaging with a MALDI matrix substance; b) acquiring a mass/mobility image of the substances in the tissue section using a MALDI mass spectrometer with built-in ion mobility spectrometer, determining and storing a map of precise masses and ion mobilities for some or all ion species in each pixel; c) extracting and solving matrix substance and small molecules of interest from the same tissue section, separating the small molecules of interest by a chromatographic or electrophoretic separation method, and acquiring the masses and ion mobilities of the extracted and separated small molecules in the mass range from 200 to 4000 Dalton using a mass spectrometer with built-in ion mobility spectrometer; d) identifying the small molecules by comparing the retention times of the substance separator, the precise masses, and the ion mobilities of the small molecule ions using reference data from a suitable database, such that a list of glycans, lipids, endogenous peptides, metabolites, pharmaceuticals, metabolites or other smaller molecules is created; and e) using the list, assigning to the entries in the mass/mobility maps of the pixels of the mass/mobility image obtained in step (b), the identity of some or all identified molecules in the list on the basis of their precise masses and their ion mobilities. The distributions of these small molecules in the thin tissue section can be then graphically presented and correspondingly investigated.

The two mass spectrometric acquisition processes of steps (b) and (c) may take hours or even days, depending on the size of the thin tissue section, the width of the scanning raster, the duration of the chromatographic separation and the number of chromatographic fractions. In commercially produced mass spectrometers, these steps are performed essentially automatically, and result in data volumes with magnitudes of gigabytes to terabytes in each case. The data from the retention/mass/mobility measurements in step (c) can be used to determine the small molecules of interest, basically by comparison with spectra derived from spectral libraries comprising separation retention times, precise masses, and collisional cross sections. The database may be filtered so that only small molecules of interest are taken into account. Depending on the differentiation of the tissue, up to 1,000 types of small molecules may be identified for a thin tissue section, but usually only a small number of molecules form the focus of the investigation.

Using a TIMS with parallel ion accumulation (FIGS. 1 and 2), ions generated by several laser shots may be collected. The MALDI laser 3 may be operated at any frequency up to 10 kilohertz. Usually it is favorable to operate the laser continuously and, in this case, the parallel accumulation is advantageous. However, in another embodiment of the invention, instead of a TIMS with parallel accumulation of ions, a simple TIMS is used. Although it lacks the advantage of an accumulation unit that may take up the ions from several laser shots, a simple TIMS may be operated with single MALDI laser shots. In such a system, 20 to 50 TIMS scans may be performed per second, using a corresponding number of laser shots.

Of great importance for avoiding assignment ambiguities is the measuring accuracy for the mass determination of the small molecules in the image. The more accurately the masses can be determined, the lower will be the number of alternative small molecules which are possible for a monoisotopic mass in the mass spectrum of an image pixel of the thin tissue section within the measurement error range. Every increase in mass accuracy in the acquisition of the mass spectrometric image of the thin section is advantageous, whether it is achieved through internal recalibration of the mass spectrometer, by operation methods achieving higher mass resolution at lower masses, or by mass spectrometers with analyzers which operate more accurately, such as orthogonal time-of-flight mass spectrometers or even Fourier transform mass spectrometers.

Although for the exemplary embodiment uses thin sections of deep-frozen tissue, the method can also be applied to thin sections of chemically stabilized tissue. Samples of tissues from clinical archives, including very old samples, stabilized by FFPE or similar methods, become accessible by this new type of molecular imaging analysis.

The invention claimed is:

1. A method for the identification and localization of molecules in a histologic tissue section that represents a first sample of a subject tissue, the method comprising:
   a) acquiring a mass spectrometric image of substances of the tissue section with a mass spectrometer having a built-in ion mobility spectrometer, and generating maps of masses and collisional cross section (CCS) values calculated from ion mobility values for molecular ions for each pixel of the image;
   b) providing a second sample of the subject tissue and extracting soluble molecules of the second sample, separating said soluble molecules and analyzing said soluble molecules using a mass spectrometer with built-in ion mobility spectrometer to acquire masses and collisional cross section values calculated from ion mobility values of molecular ions formed from the soluble molecules;
   c) identifying molecules in the second sample of the subject tissue by comparing retention times of a method used for said separating of the soluble molecules, the masses and the collisional cross section values of the ions formed from the soluble molecules with reference data, and creating a list of identified molecules from the second sample of the subject tissue; and
   d) assigning identified molecules in the list to entries in said mass/CCS maps generated in step (a) according to mass and collisional cross section.

2. The method according to claim 1, wherein the second sample of the subject tissue is a second tissue section of the subject tissue.

3. The method according to claim 1, wherein the second sample of the subject tissue comprises a plurality of tissue sections of the subject tissue.

4. The method according to claim 1, wherein the second sample of the subject tissue comprises a piece of the subject tissue larger than the tissue section.

5. The method according to claim 1, wherein the tissue section, after acquisition of the mass spectrometric image, is used as the second sample of the subject tissue.

6. The method according to claim 1, wherein the ions formed from the soluble molecules are fragmented prior to being analyzed mass spectrometrically, and the identification of molecules in step (c) is based on said retention times, said masses and collisional cross section values of the ions formed from the soluble molecules, and a fragment ion spectrum of fragmented soluble molecules.

7. The method according to claim 1, wherein targeted molecule species are glycan or lipid groups in complex compounds of the subject tissue, and wherein an enzymatic digestion of glycocomplexes or lipidocomplexes of the first and second samples of the subject tissue is performed to cleave glycans or lipids from the complex compounds, said enzymatic digestion being done for the histological tissue section in a position-conserving manner.

8. The method according to claim 1, wherein said acquiring of a mass spectrometric image is performed using ionization by matrix-assisted laser desorption (MALDI).

9. The method according to claim 1, wherein said separating of said soluble molecules is performed using liquid chromatography or capillary electrophoresis.

10. The method according to claim 1, wherein analyzing said soluble molecules using a mass spectrometer includes ionization by electrospray ionization (ESI).

11. The method according to claim 1, wherein, after separating said soluble molecules, separated fractions are prepared together with a matrix substance as individual samples on one or more matrix-assisted laser desorption ionization (MALDI) sample support plates, and said analyzing of said soluble molecules using a mass spectrometer includes ionization with a MALDI ion source.

12. The method according to claim 1, wherein a distribution of a molecule species of interest on the histological tissue section is investigated with respect to homogeneously covered areas of those species, and wherein isolated species are omitted from said mass/CCS maps.

13. The method according to claim 1, wherein a plurality of tissue sections of the subject tissue are analyzed in step (a), and steps (b) and (c) are only carried out once, with the list of identified molecules obtained in step (c) being used for assignment of molecules identified in step (d) to species of mass/mobility images of each of said plurality of tissue sections.

14. The method according to claim 1, wherein said histological tissue section is a chemically-stabilized tissue section.

* * * * *